United States Patent [19]

Pearson et al.

[11] Patent Number: 4,755,459

[45] Date of Patent: Jul. 5, 1988

[54] DETECTION OF GONOCOCCAL INFECTIONS USING MONOCLONAL ANTIBODIES

[75] Inventors: Terry W. Pearson, Victoria; Malcolm B. Perry, Ottawa, both of Canada

[73] Assignee: Canadian Patents and Development Limited, Ottawa, Canada; by said Malcolm B. Perry

[21] Appl. No.: 742,853

[22] Filed: Jun. 10, 1985

[30] Foreign Application Priority Data

Jun. 14, 1984 [CA] Canada ................................ 456571

[51] Int. Cl.$^4$ .................... G01N 53/00; G01N 33/53; C12Q 1/04; C12R 1/36
[52] U.S. Cl. ......................................... 435/7; 435/34; 435/35; 435/39; 435/253; 435/871; 436/511; 436/545; 436/546; 436/811; 530/387
[58] Field of Search .............. 436/548, 545, 546, 811, 436/511; 435/35, 34, 7, 39, 253, 871; 530/387

[56] References Cited

U.S. PATENT DOCUMENTS 4,115,543  9/1978  Wallace et al. .................... 436/511

OTHER PUBLICATIONS

Apicella et al, Infection and Immunity, vol. 34. No. 3, Dec. 1981, pp. 751-756.
Diena et al, Can. J. Microbiol., vol 24, 1978, pp. 117-123.
Sugasawara et al, Infection and Immunity, vol. 42, No. 3, Dec. 1983, pp. 863-868.

Primary Examiner—Sidney Marantz
Assistant Examiner—Florina B. Hoffer
Attorney, Agent, or Firm—Alan A. Thomson

[57] ABSTRACT

Monoclonal antibodies specific to *Neisseria gonorrhoeae* lipopolysaccharide components having no cross-reactivity with *N. meningitidis* have been produced and found useful in the diagnosis of the presence of *N. gonorrhoeae*.

7 Claims, No Drawings

DETECTION OF GONOCOCCAL INFECTIONS USING MONOCLONAL ANTIBODIES

BACKGROUND TO THE INVENTION

This invention concerns the development of means for the diagnosis of the presence of *Neisseria gonorrhoeae* employing monoclonal antibodies.

Detection of *N. gonorrhoeae* has been the subject of much research effort as exemplified by R. B. Wallace et al, Canadian Pat. No. 1,083,480 (corresponding U.S. Pat. No. 4,115,543); A. S. Armstrong's U.S. Pat. No. 4,332,890; H. C. McDonald's U.S. Pat. Nos. 4,248,964 and 4,254,218; H. H. Weetall's U.S. Pat. No. 4,245,038. Antigenic, immunogenic complexes obtained from the cell surface of *N. gonorrhoeae* are the subject of Y. D. Karkhanis' U.S. Pat. No. 4,288,557, who also describes a process for the solubilization of gonococcal antigens in U.S. Pat. No. 4,330,623. Recent developments in monoclonal antibody technology include a test method to differentiate *Herpes simplex* virus type 1 and type 2 described by B. Hampar et al in U.S. Pat. No. 4,430,437.

SUMMARY OF THE INVENTION

This invention concerns methods and kits for the detection of *N. gonorrhoeae* employing monoclonal antibodies.

A method of detecting the presence of *N. gonorrhoeae* may comprise:

(a) providing a sample suspected of containing said *N. gonorrhoeae*, (b) contacting said sample with at least one monoclonal antibody to *N. gonorrhoeae* antigens, particularly *N. gonorrhoeae* lipopolysaccharide. Monoclonal antibody particularly useful in the above methods may be produced by hybridoma cells, the spleen-derived parent of which has been induced by antigenic R-core lipopolysaccharide derived from the cell surface of *N. gonorrhoeae*, said antibody being capable of specifically binding to at least one antigenic determinant of *N. gonorrhoeae*.

An additional step (c) may be employed. Step (c) may comprise contacting the product of step (b) with means to assist detection of interactions between the sample and the monoclonal antibodies. For example, such means to assist detection may be selected from the group consisting of a radiolabel, a fluorescence label and an enzyme label. The means to assist detection may be an immunoglobulin that binds to the monoclonal antibodies.

A monoclonal antibody may be produced by hybridoma cells, the spleen-derived parent of which has been induced by antigenic lipopolysaccharide, especially R-core lipopolysaccharide, derived from the cell surface of *N. gonorrhoeae*, said antibody being capable of specifically binding to at least one antigenic determinant of *N. gonorrhoeae*.

A kit to detect the presence of *N. gonorrhoeae* may comprise:

(a) a reagent containing at least one monoclonal antibody of the type described above, and (b) means to assist detection of interactions between *N. gonorrhoeae* antigens and at least one monoclonal antibody.

Such means to assist detection may have a label selected, for example, from the group consisting of a radiolabel, a fluorescence label and an enzyme label. Such means to assist detection may be an immunoglobulin that binds to the monoclonal antibodies.

DETAILED DESCRIPTION OF THE INVENTION

Abbreviations used: LPS, lipopolysaccharide; ELISA, enzyme-linked immunosorbent assay; KDO, 3-deoxy-D-manno-octulosonic acid; I.P., intraperitoneally; PBS, phosphate buffered saline; I.V., intravenously; GC6, strain In21GC6.

Bacterial strains

Strains of *N. gonorrhoeae* employed include GC6 and G9, employed for purification of LPS, and strains of V1 and V2. *N. meningitidis* strains VC2 and VC7 were used for initial specificity screening. All Neisseria were stored at −70° C. in nutrient broth containing 20% defined supplement and 0.001% ferric nitrate.

Bacterial lipopolysaccharides

GC6 and G9 strains of *N. gonorrhoeae* grown in the type 4 colony form were harvested directly from GC agar plates and the LPS were obtained using a hot phenol-water extraction procedure, described by M. B. Perry et al, Can. J. Biochem. 53, 523, 1975. The LPS obtained had a composition similar to that found for typical "R" type LPS of gram negative bacteria. *Salmonella typhimurium* LPS SA22 (gal E) and LT2, *Aeromonas salmonicida* LPS, and *Escherichia coli* LPS were employed as controls.

Formation of monoclonal antibodies

Immunization of mice for cell fusion. Female BALB/c mice were employed. Four mice of 10–12 weeks of age were injected I.P. with 50 g purified R-core LPS (GC6 or G9) in PBS. Twenty-one days later, 2 mice were injected I.V. with 20 μg LPS in PBS. Three days later, the spleens were removed, cell suspensions were prepared, pooled and used for cell fusion.

Cell fusion and cloning. Spleen cells for gonococcal LPS-immunized mice were fused to X63Ag8.6.5.3 parental myeloma cells or to SP2/0 parental myeloma cells using polyethylene glycol. The SP2/0 cells were a subclone selected for high fusion efficiency and successful monoclonal antibody production. Supernatants from fusion wells were tested for antibodies to gonococcal LPS using solid-phase radioimmunometric assays as described below. Cells from positive wells were cloned by limiting dilution as described by V. Oi and L. P. Herzenberg in Collected Methods in Cellular Immunology (ed. B. B. Mishell and S. M. Shiigi), W. H. Freeman, San Francisco (1980). After selection of positive clones and recloning, selected myeloma hybrids were grown as ascites in pristane treated mice in order to obtain large quantities of monoclonal antibodies for further analysis.

Antigenicity of gonococcal R-core LPS. Fourteen days after a single I.P. injection of 50 μg GC6 or G9 LPS in complete Freund's adjuvant, mice were bled from the tail and their sera titrated against homologous LPS using radioimmunometric assay. All animals showed titers of greater than 1/1000. Two mice immunized with GC6 LPS and two immunized with G9 LPS were then selected and boosted I.V. with 20 μg LPS in saline and fusions carried out as described above.

Cell fusion and selection of hybrids. The first fusion was performed with GC6 LPS-immunized mouse spleen. All 48 wells showed growth of hybrids. Supernatants from seventeen of these were positive for GC6 LPS when tested in solid-phase radioimmunometric assay. Hybrids from these wells were grown in 30 ml flasks and retested. Ten remained positive and the hybrids were cloned by dilution. Clones from five of these produced antibody to the GC6 LPS. The antibodies from one of these, GC6 1/40.2, bound strongly to the GC6 LPS (20 times background) and was cloned again. The doubly cloned hybrid GC 1/40.2.30 was selected for further analysis. The other hybridomas from this fusion were kept as single clones.

The second fusion used spleen cells from G9 LPS-immunized mice. Again all of 48 wells showed growth of hybrids. Supernatants from 30 of these wells contained antibodies which bound to G9 LPS. Eight of these were selected (4 giving high cpm bound, 2 middle and 2 low) and the hybridomas cloned by dilution. Clones from 5 of these produced antibody to G9 LPS. All were cloned again and remained stable.

All stable hybridomas were given as ascites fluids. The cells were removed by centrifugation and frozen in liquid nitrogen approximately $5 \times 10^7$ cells/ml in 90% fetal calf serum/10% dimethylsulfoxide. All were successfully grown after thawing. The cell-free ascites fluids were filtered through a $0.45\mu$ millipore, sodium azide added to 0.01% final concentration and frozen at $-20°$ C. until used for further testing.

Solid-phase radioimmunometric assays. Polyvinyl chloride microwells were incubated overnight at 4° C. with 0.2 ml of 25 Mg/ml LPS in coating buffer (carbonate-bicarbonate pH 9.6). Wells were washed 3 times using PBS-Tween [trademark] buffer (PBS pH 7.4 containing 0.2% Tween [trademark] 20) and 0.1 ml hybridoma supernatants or ascites dilutions added to the wells. After 2 hours at 20° C., the wells were washed 3 times with PBS-Tween [trademark] and 0.1 ml PBS-Tween [trademark] containing 100,000 counts per minute (cpm) of $^{125}$I-labelled F(ab')$_2$ portions of goat anti-mouse IgG F(ab')$_2$ added to each well. After a further 2 hours incubation, the wells were washed, dried, cut with a hot wire and counted for one minute in a Beckman Biogamma 8000 [trademark] scintillation spectrometer. Control wells received either tissue culture supernatants or dilutions of ascites fluids from the myeloma cell line X63-Ag8 which secretes an IgG, K immunoglobulin of unknown specificity. In screening assays, supernatants were considered positive if counts per minute bound were twice those found in control wells.

Immunofluorescence assays. Monoclonal antibodies were selected for surface binding to *N. gonorrhoeae* using indirect immunofluorescence. Fresh cultures of *N. gonorrhoeae* and *N. meningitidis* were used to prepare slides. These were air dried onto acid-cleaned slides and 0.02 ml of ¼ dilutions of tissue culture supernatants or of 1/100 dilutions of ascites fluids (in PBS) containing monoclonal antibodies were added to a 1 cm circular area of bacterial cells. After 30 min incubation at room temperature, the slides were washed by three successive immersions in PBS/1% BSA in Coplin [trademark] jars and 0.02 ml of a 1/20 dilution of rhodamine-labelled goat anti-mouse IgG was added to the circular area of cells. After 30 min incubation, the slides were washed three times by immersion in 100 ml of PBS and a drop of mounting medium used to fix a coverslip in place. Clear nail polish was used to secure the coverslip and the slides were examined immediately using a Standard Zeiss [trademark] microscope fitted with an epifluorescence attachment and a Neofluor [trademark] 63x oil immersion objective.

The results are shown in Table 1. Each hybridoma secreted antibody specific for the antigen used to immunize the mice prior to fusion. In all cases both tissue culture supernatants and ascites fluids from a given hybrid gave identical results. Supernatants from the singly cloned hybridomas from the first fusion were all negative in this assay as they gave low binding to all species of LPS (data not shown). These were not studied further.

All positive ascites fluids were titrated against the two gonococcal R-core LPS molecules (GC6 and G9) and were tested in indirect immunofluorescence for surface binding to various gonococci and meningococci (Table 2). All monoclonal antibody ascites fluids had high titres against the homologous LPS. Only at low dilutions was cross-reactivity on the non-homologous LPS observed. Titration of the same ascites fluids against solid-phase adsorbed human albumin or human transferrin showed similar non-specific binding at low ascites dilutions. For this reason, ascites dilutions of 1/1000 or greater were used in further testing for specificity although undiluted tissue culture supernatants were used for initial immunofluorescence testing. All of the monoclonal antibodies bound to the surface of both strains of *N. gonorrhoeae* tested in immunofluorescence assays. Binding to *N. meningitidis* strains was uniformly negative.

Isotype determinations. Monoclonal antibody isotypes were determined by solid-phase radioimmunometric assay using homologous LPS as solid-phase bound antigen and a 1/1000 dilution of monoclonal antibody ascites fluid as first antibody. Second antibodies were affinity-purified $^{125}$I-labelled goat anti-mouse IgM ($\mu$ chain) or $^{125}$I-labelled goat

TABLE 1

Binding[a] of anti-gonococcal LPS monoclonal antibodies to LPS from several bacterial species

| Hybridoma[c] | LPS[b] | | | | | |
|---|---|---|---|---|---|---|
| | R-core GC6 | R-core G9 | S. typhmurium | | A. salmonicida | E. coli |
| | | | SA22 | LT2 | | |
| GC61/40.2.30 | $10^6$ | $10^3$ | — | — | — | — |
| G91/12.1.3 | $10^3 - 10^6$ | $10^6$ | — | — | — | — |
| G91/15.1.12 | $10^3$ | $10^5$ | — | — | — | — |
| G91/23.17.6 | $10^3$ | $10^6$ | — | — | — | — |
| G91/26.23.11 | $10^3$ | $10^5$ | — | — | — | — |
| G91/28.18.23 | $10^3$ | $10^6$ | — | — | — | — |

TABLE 1-continued

Binding[a] of anti-gonococcal LPS monoclonal antibodies to LPS from several bacterial species

| | LPS[b] | | | | | |
|---|---|---|---|---|---|---|
| | | | S. typhmurium | | | |
| Hybridoma[c] | R-core GC6 | R-core G9 | SA22 | LT2 | A. salmonicida | E. coli |
| TC6/42.6.4[d] | — | — | — | — | — | — |

[a]Titre in solid-phase radioimmunometric assay. $^{125}$I-anti-murine light chain reagent was used to detect antibodies binding to LPS. Minus signs (—) indicate binding occurred only at dilutions of $10^2$ or less.
[b]LPS from all species was used at 25 μg/ml to coat the microwells.
[c]Ascites fluids diluted 1/10 — 1/10$^7$ were used from each hybrid.
[d]Control hybridoma which secretes antibody specific for an antigen on African tryponosomes.

TABLE II

Titration[a] of anti-gonococcal LPS monoclonal antibodies and specificity testing by indirect immunofluorescence

| Monoclonal antibody | Titre[b] | | Immunofluorescence[c] | | | |
|---|---|---|---|---|---|---|
| | LPS GC6 | LPS G9 | N. gonorrhoeae V1 | N. gonorrhoeae V2 | N. meningitidis VC2 | N. meningitidis VC7 |
| GC6 1/40.2.30 | $10^5$ | $10^1 - 10^2$ | + | + | — | — |
| G9 1/12.1.3 | $10^6$ | $10^2 - 10^3$ | + | + | — | — |
| G9 1/15.1.12 | $10^4$ | $10^2$ | + | + | — | — |
| G9 1/23.17.6 | $10^6$ | $10^1$ | + | + | — | — |
| G9 1/26.23.11 | $10^6$ | $10^1 - 10^2$ | + | + | — | — |
| G9 1/28.18.23 | $10^6$ | $10^2 - 10^3$ | + | + | — | — |
| X63.Ag8 (control) | $10^2$ | $10^1 - 10^2$ | — | — | — | — |

[a]Ten-fold dilutions of ascites fluids (starting at 1/100) were tested in solid-phase radioimmunometric assay
[b]Highest dilution of ascites fluids which gave binding twice that of control ascites
[c]Indirect surface immunofluorescence on intact bacteria using undiluted tissue culture supernatants as first antibody anti-mouse IgG (γ chain). By using high dilutions of ascites containing monoclonal antibodies in this assay, accurate determinations of isotypes can be made without interference from contaminating antibodies present in the ascites fluids.

Competitive inhibition enzyme-linked immunosorbent assays. A competitive inhibition ELISA was developed for the analysis of antibody-LPS interactions. Various mono- and disaccharides or constituent portions of gonococcal LPS were used as inhibitors of a specific ELISA reaction.

Purified LPS (0.1 ml, 20 μg/ml in 0.01M carbonate buffer pH 9.5) was added to microtiter plates. To this was added 0.1 ml of 0.02M MgCl$_2$. The plates were incubated for 2 h at 37° C. and then washed with 0.02M MgCl$_2$. The various constituent sugars or other constituent portions of the gonococcal R-core LPS were diluted out directly in the plates in ELISA buffer (100 μl, 0.01M PBS with 0.01% Tween [trademark] 20, 0.01% bovine serum albumin and 0.002M MgCl$_2$). All assays were done in triplicate. To this was added a predetermined antibody dilution (0.1 ml). Control wells received buffer only in place of inhibitor. The plate was incubated for 1 hr at 37° C. and then washed with ELISA buffer 3 times. Anti-immunoglobulin conjugated to horseradish peroxidase (0.2 ml) at a predetermined dilution was added to the wells and incubated for 1 h at 37° C. The plate was then washed three times with ELISA buffer. Substrate (0.2 ml, O-phenylenediamine 8 mg, 30% H$_2$O$_2$ 5 μl, in 20 ml citrate buffer pH 5.6) was added and incubated for 2 h at room temperature in the dark. The plates were read on an ELISA reader at 450 nm.

All of the monoclonal antibodies bound to the homologous intact LPS and to the isolated R-core LPS as expected. All antibodies were also 100% inhibited by the disaccharide lactose. Two of the antibodies were specifically inhibited by both lactose and galactose. One of the monoclonal reagents were inhibited by all of the core sugars and by arabinose and maltose. None of the antibodies bound to LPS purified from other bacterial species (E. coli, A. salmonicida, S. typhimurium) or to LPS on other intact organisms (N. meningitidis and nine other Neisseria species, S. aureus, E. coli) several of which are known to have lactose, glucose, galactose and N-acetylglucosamine as LPS constituents.

The monoclonal antibodies isolated and characterized above may thus be employed in kits and in diagnostic procedures to test for the presence of N. gonorrhoeae in samples by, for example, agglutination, radioisotope labelling, fluorescence labelling, or enzyme-linked labelling techniques such as RIA and ELISA.

We claim:

1. A method of detecting the presence of N. gonorrhoeae comprising:
   (a) providing a sample suspected of containing said N. gonorrhoeae, and
   (b) contacting said sample with at least one monoclonal antibody to N. gonorrhoeae R-core lipopolysaccharide antigens, the antibody having no cross-reactivity with N. meningitidis,
   (c) detecting the binding of the monoclonal antibody of step (b) to N. gonorrhoeae wherein said binding is an indication of the presence of N. gonorrhoeae.

2. The method of claim 1 wherein said monoclonal antibody has been produced by hybridoma cells, comprising a cell capable of producing antibodies against said R-core lipopolysaccharide derived from the cell surface of N. gonorrhoeae, said antibody being capable of specifically binding to at least one antigenic determinant of N. gonorrhoeae without binding to any N. meningitidis antigenic determinant.

3. The method of claim 1 wherein step (c) comprises contacting the product of step (b) with a labelled immunoglobulin that binds to the monoclonal antibodies.

4. The method of claim 3 wherein said label is selected from the group consisting of a radiolabel, a fluorescence label and an enzyme label.

5. A kit to detect the presence of N. gonorrhoeae comprising:

(a) a container containing a reagent having at least one monoclonal antibody raised against the R-core lipopolysaccharide of *N. gonorrhoeae* and having no cross-reactivity with *N. meningitidis,* and (b) a container containing a label for the detection of interactions between *N. gonorrhoeae* antigens and said monoclonal antibody.

6. The kit of claim 5 wherein said label is selected from the group consisting of a radiolabel, a fluorescence label and an enzyme label.

7. The kit of claim 5 wherein said label is an immunoglobulin that binds to the monoclonal antibodies.

* * * * *